United States Patent
Svadovskiy

(10) Patent No.: US 6,666,213 B2
(45) Date of Patent: Dec. 23, 2003

(54) METHOD FOR TREATING GLAUCOMA

(76) Inventor: Aleksandr Igorevich Svadovskiy, KV.24, Korp.2,D.4 UL.Bolshaya Cherkizovskaya, Moscow (RU), 105187

( * ) Notice: Subject to any disclaimer, the term of this patent is extended or adjusted under 35 U.S.C. 154(b) by 3 days.

(21) Appl. No.: 10/160,891

(22) Filed: Jun. 3, 2002

(65) Prior Publication Data
US 2003/0034038 A1 Feb. 20, 2003

(30) Foreign Application Priority Data
Aug. 15, 2001 (RU) ......................................... 2001122797

(51) Int. Cl.⁷ ............................................... A61B 19/00
(52) U.S. Cl. ......................................... 128/898; 604/8
(58) Field of Search ........................................ 128/898

(56) References Cited

U.S. PATENT DOCUMENTS 4,269,691 A  5/1981 Deborski ................ 204/290 R
4,750,901 A * 6/1988 Molteno ........................ 604/8
5,468,221 A * 11/1995 Schoner ........................ 604/8

OTHER PUBLICATIONS

International Search Report PCT/RU 00/00208.

* cited by examiner

Primary Examiner—David H. Willse
Assistant Examiner—Thomas J Sweet
(74) Attorney, Agent, or Firm—J. Herbert O'Toole; Nexsen Pruet Jacobs & Pollard, LLC

(57) ABSTRACT

The method for treating glaucoma, consisting in that an osteoplastic trepanation in the frontal region above the affected eyeball, followed by effecting an extradural approach to the superior orbital wall. Next the aqueous humour is let to flow out by effecting a resection trepanation of the superior orbital wall in order to establish a contact between the edematous perieyeball fat and the dural surface.

3 Claims, 2 Drawing Sheets

METHOD FOR TREATING GLAUCOMA

TECHNICAL FIELD

Figure 2:
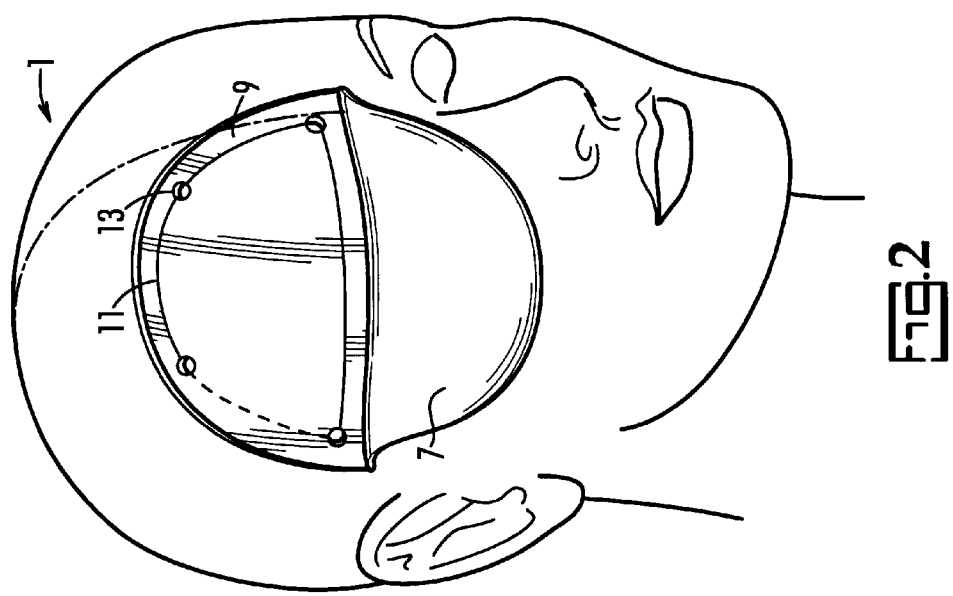
Figure 1:
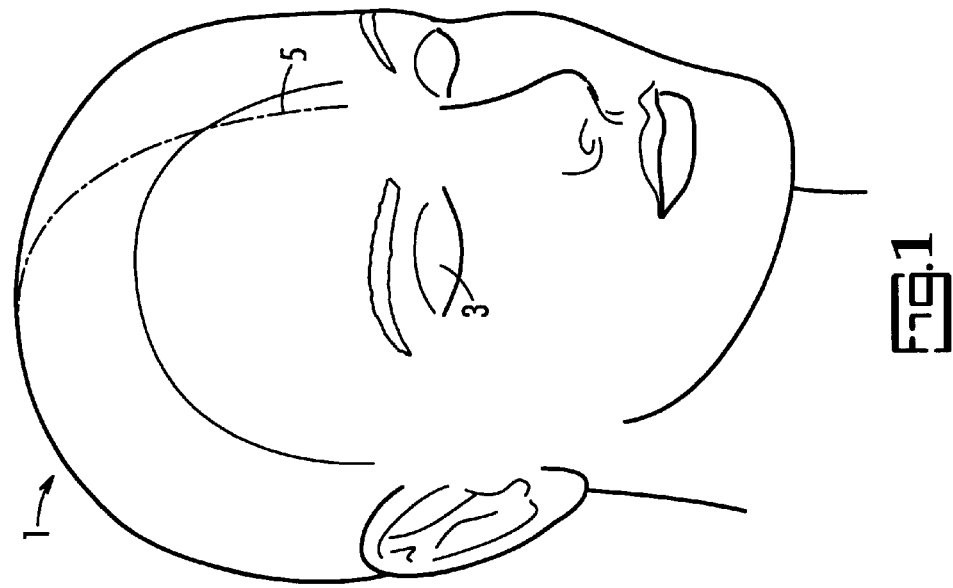
Figure 4:
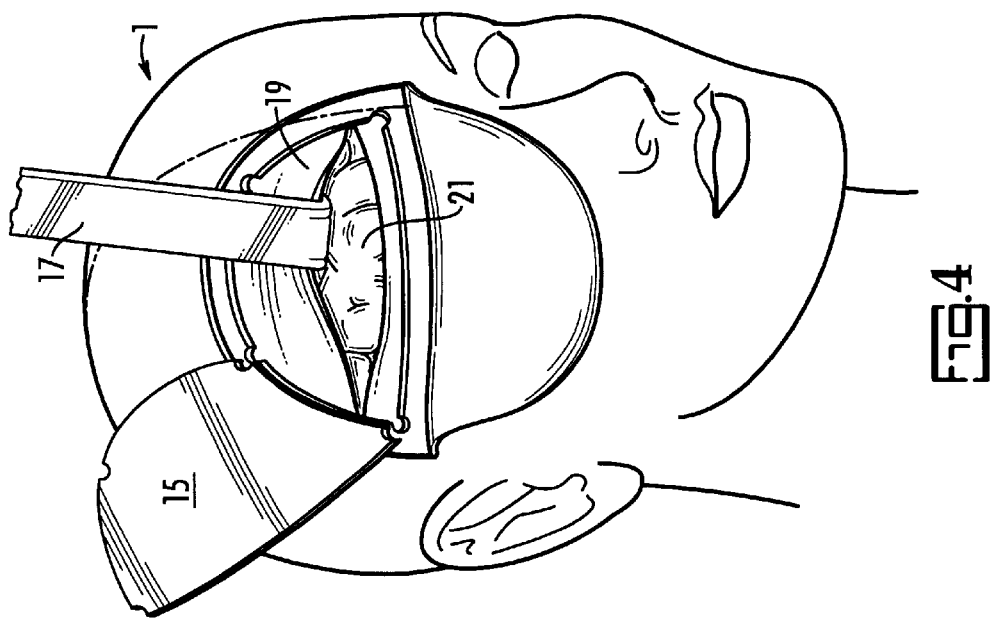
Figure 3:
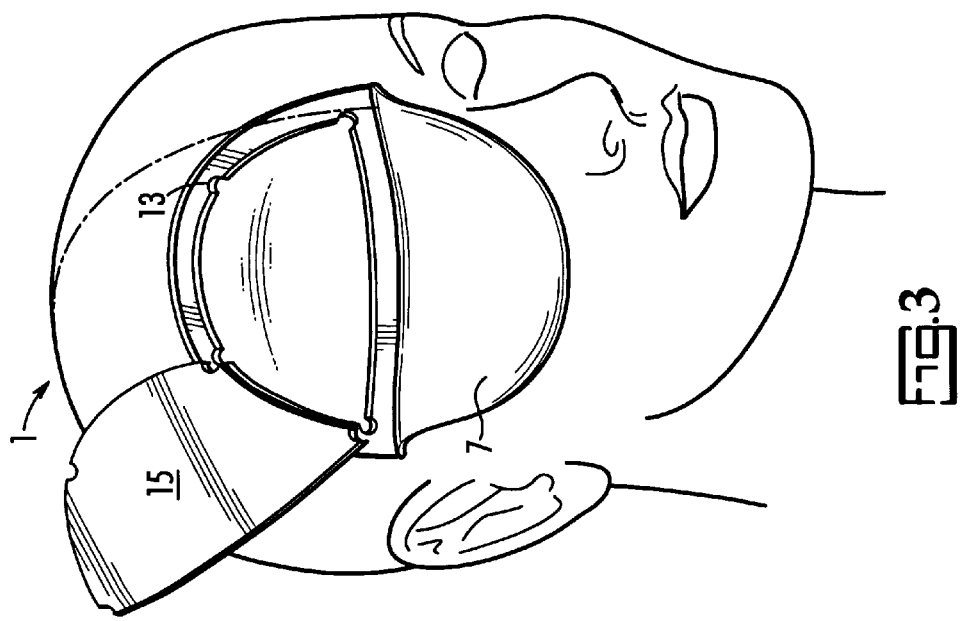

The present invention relates in general to medicine, more specifically it concerns a method for treating glaucoma.

BACKGROUND ART

The present invention can find application in surgery, more particularly, in neurosurgery for treating the various kinds of glaucoma.

It is known commonly that in a healthy eye a definite intraocular pressure (18 to 22 mm Hg) is constantly maintained due to a balance between the inflow and outflow of the intraocular fluid. In a glaucomatous eye circulation of the intraocular fluid is disturbed, with the result that the fluid (the so-called aqueous humour) is accumulated and the intraocular pressure starts rising. As a result, the optic nerve gradually atrophies, the blood supply of the eye is disordered, the eyesight deteriorates incessantly so that if no medical countermeasures are taken, the outcome may be complete blindness.

Traditional, classic methods of conservative and surgical treatment of open/narrow-angle glaucoma are extensively known in ophthalmologic practice to comprise medicines, i.e., in drop forms (conservative treatment) capable of reducing abnormally high intraocular pressure, surgical intervention, i.e., sclerectomy aimed at activation of uveoscleral path of outflow, including laser-aided surgery, and some other surgical operations [cf. the paper by G. G. Kornilaeva, journal "Vestnik oftalmologhii" (Ophthalmologic Bulletin), Moscow, 1999; Collected Proceedings of the First Eurasian Conference on Ophthalmology, Ekaterinburg, 1998 (in Russian)]

Modern conservative and/or surgical treatment of glaucoma is aimed at stabilizing and reducing intraocular pressure, stopping further eyesight deterioration and atrophy of the optic nerve. In the event of progressive atrophy of the optic nerve resort is made to transcutaneous electrostimulation, repeated classic surgical intervention mentioned above, or attempts are made of surgical revascularization of optic nerve using "Alloplant" technique [cf. Muldashev E. R. et al., European Association for Vision, Spain, 1988; Symposium "Urgent problems of Clinical Ophthalmology", Cheliabinsk, 1999 (in Russian)]

However, despite a full complex therapy having been carried out, a certain proportion of the treated patients (20 to 30%) exhibit complete atrophy of either or both of the optic nerves and hence blindness occurs. Sometimes such a terminal stage of loss of vision is accompanied by very severe pain in one eye (more rarely in both eyes) which requires surgery for exenteration of the eyeball followed by replacing it with a prosthetic one [cf. the textbook "Ophthalmology" by E. I. Kovalevski, Moscow, Meditsina Publishers, 1995 (in Russian).]

One more method for treating glaucoma is known, namely, mechanical or laser-aided sclerectomy (non-penetrating deep sclerectomy). Once performed, said surgery results in restoring the natural balance of the intraocular fluid.

According to the published data, as many as one-third of a total number of the blind lost their vision due to glaucoma (cf. the textbook "Tolerant and Intolerant Pressure in Glaucoma", Moscow, 1991).

Etiological factors of glaucoma development are atherosclerosis and diabetes mellitus; other hereditary factors also play some part as well.

Known in the present state of the art is a method for treating glaucoma (cf. RU patent #2,021,794, C1), consisting in practicing an outflow of the aqueous humour. The surgical techniques resides in dilating the lumen of the Schlemm's canal using a metal thread 0.05 mm thick having shape memory effect, with a view to improving the natural physiological outflow between the anterior and posterior chambers of the eye. The method in question for treating glaucoma makes no provision for neurosurgical intervention.

However, said method for treating glaucoma rarely results in completely normalizing the intraocular pressure and stabilizing the condition of the ocular fundus (that is, elimination of the glaucomatous excavation of the optic disk). Furthermore, notwithstanding the effect of stabilizing the intraocular pressure attained due to the treatment using said method, the latter fails to stabilize further atroplication of the optic nerve, nor can said method prevent further reduction of visual acuity and deterioration of the visual fields as far as complete blindness occurs. In badly neglected cases of the glaucomatous process, the transudate (i.e., the aqueous humour) pervades the oculomotor muscles and perieyeball fat. Attempts to enhance natural outflow through the Schlemm's canal is obviously inadequate since the carrying capacity of said expanded canal is but too low due to its small area even when enlarged by said metal thread. The lesson is clear that establishing an increased intraocular outflow alone cannot arrest progressive atrophy of the optic nerve.

Hence the method for treating glaucoma discussed above fails to establish a new path for the aqueous humour to outflow outwards the eyeball with an adequate area of drainage of the aqueous humour nor can said method provide stabilization of the clinical aspect of the optic nerve atrophy or its regression followed by increasing the visual function. Ultimately, the efficacy of glaucoma treatment using the traditional methods is rather low.

BRIEF SUMMARY OF THE INVENTION

It is an object of the present invention to provide a method for treating glaucoma, said method being capable of attaining, due to establishing a new path for the aqueous humour to outflow beyond the limits of the eyeball during neurosurgical intervention with an adequate area for the aqueous humour to drain off, stabilization of the clinical aspect of atrophy of the optic nerve, or regression of said atrophy, with the resultant increase in the visual function, thus adding to the efficacy of glaucoma treatment.

Said object is accomplished due to the fact that in a method for treating glaucoma consisting in outflow of the aqueous humour, according to the invention, an osteoplastic trepanation is performed in the frontal region above the affected eyeball, an extradural approach to the superior wall of the orbit is performed, while outflow of the aqueous humour is carried out by way of resection trepanation of the superior wall of the orbit in order to provide a contact between the edematous perieyeball fat and the dural surface.

It is expedient that in the event of profuse bleeding from the perieyeball fat resulting from resection trepanation of the superior orbit wall, a biological protector be positioned in the space between the superior wall of the orbit and the dura mater.

It is likewise reasonable that the aforementioned osteoplastic trepanation in the frontal region above the affected eyeball be preceded by an additional examination by way of high-resolution magnetic-resonance imaging.

The present invention allows of attaining higher treatment efficacy and makes possible curing a greater amount of patients than the traditional treating methods, this being due to the fact that despite all advances of microsurgical and pharmacological treatment methods, a certain proportion of the patients treated by the heretofore-known traditional methods cannot be cured.

The present invention enables the field of its application to be extended, since the treatment method proposed therein is applicable for treating any forms of glaucoma save the congenital one characterized by progressive atrophy of the optic nerve.

The present method for treating glaucoma is also applicable for both open-angle and narrow-angle glaucoma, as well as in bilateral glaucoma. In such a situation one-time bilateral resection of the superior wall of the orbit is indicated. Should a one time surgery be impossible for some reason, two consecutive neurosurgical interventions are performed first on the one of the orbits, then on the other, at an interval of two or three months.

Hence the present method for treating glaucoma due to the provision of a new path for the aqueous humour to flow outwards of the eyeball ensures stabilization of the clinical aspect of atrophy of the optic nerve or regression of said atrophy accompanied by increasing the visual function, which adds to the efficacy of the glaucoma treatment process.

DETAILED DESCRIPTION OF THE INVENTION

In what follows the present invention is illustrated in some specific exemplary embodiments thereof.

The herein disclosed method for treating glaucoma consists in that an osteoplastic trepanation is performed in the frontal region above the effected eyeball and an extradural approach to the superior wall of the orbit is carried out, whereupon the aqueous humour is let to flow out beyond the limits of the eyeball. To this effect a resection trepanation of the superior wall of the orbit is performed in order to establish a contact between the edematous perieyeball fat and the dural surface. Hence said resection trepanation of the superior orbital wall established direct anastomosis between the edematous perieyeball fat that prolapses into the osseous defect and the exterior dural surface, said anastomosis establishing drainage of the excess aqueous humour which has been accumulated in the eyeball, into the dura mater and further into the venous system of the head.

Magnetic-resonance imaging of glaucoma patients revealed a pathological amplification of the increased activity signal in the orbit, more exactly, in the perieyeball fat (condition T2). The aforesaid increased activity signal gives evidence of an increased water content of the perieyeball fat. In addition, there was found a considerable increase in the diameter of the intraorbital portion of the optic nerve as far as the *canalis opticus*. This in turn is indicative of an edema of the optic nerve and of its being impacted in the axial occipital direction. On the healthy eye (in case of unilateral glaucoma) subjected to magnetic-resonance tomography the picture of the orbit was regarded as normal. Hence it seems that a self-impaction of the optic nerve occurs, that is, impaction of its intraorbital portion due to edema caused by disordered circulation of the aqueous humour in the eyeball. Hence an upset outflow of the aqueous humour in the eyeball results ultimately in atrophy of the optic nerve and in blindness.

The herein-proposed method for treating glaucoma is based on osteal decompression of the superior orbital wall, i.e., the roof of the orbit which also serves as the base of the anterior cranial fossa, with a view to establish immediate anastomosis between the edematous perieyeball fat and the exterior dural surface. As the dura mater possesses some resorbability it is capable of "releasing" the eyeball from an abnormally high water content by active water absorption. As it has been stated before in discussing the disclosed method, the treatment consists in performing a neurosurgical intervention. The surgery involves a standard osteoplastic trepanation (aimed at gaining access to the cavity of skull) in the frontal region on the side adjacent to the glaucoma-affected eyeball [cf. "Textbook of Neurosurgery" by I. S. Irger, 1972, Moscow, Meditsina Publishers (in Russian)]. Thereupon, an extradural approach to the superior orbital wall is carried out, sufficient for a resection trepanation of said wall to effect, involving the backward traction towards the frontal pole. Then a standard resection trepanation is performed by making a burr hole to prevent damage to the frontal sinus, whereupon said hole is enlarged using bone nippers until a trepanation window is obtained. The overall dimensions of such a trepanation window usually measure 2.5×3.0×2.5 cm. As a rule, edematous fat is likely to prolapse into the thus-established trepanation defect. Finally, an osteplastic graft is laid onto site, whereupon skin stitches are applied.

In the early postoperative period, i.e., within two or three weeks after surgery, an ophthalmologic study detected disappearance of the edema or its regression (reduction), discoloration of the optic disk, reduced hyperemia of the retinal veins, and improved visual acuity by 0.05–0.1. Further observation of the ophthalmologic functions for a period of 3–6 months demonstrated at least stabilization of visual acuity and of the condition of the ocular fundus, and even the reversal of progressive changes in the ocular fundus, as well as improved visual acuity. In a control magnetic-resonance imaging of the orbit involving displaying the optic nerve there is observed reduction of absolute values of the increased activity signal (in T2 condition) from the perieyeball fat, restoring normal diameter of the intraocular optic nerve portion comparable with the diameter of the contralateral nerve.

In the case of post-decompression situation of the superior orbital wall following surgery for resection trepanation of said orbital wall and when profuse bleeding from the prolapsing perieyeball fat is observed, a biological protector is made use of, to be placed in the space between the superior wall of the orbit and the dura mater. Used as said protector may be the commonly known hemostatic sponge (cf. the journal "Neurosurgery", June 1996, vol.38 #6, Williams and Wilkins, pp.6–15), or a tachocomb [cf. "Lesion of the Brain", in: Proceedings of the Fifth International Symposium held in Saint-Petersburg, 1999, p.486 (in Russian)]. Furthermore, with a view to assessing the status of the perieyeball fat and the diameter of the optic nerve, prior to performing the aforesaid osteoplastic trepanation in the frontal region above the affected eyeball an additional examination is carried out in the form of a standard magnetic-resonance imaging.

The present method of treating glaucoma was tested under clinical conditions. Clinical trials were conducted at the neurological and neurosurgical clinic "Neuroaesculap" in Moscow for treating patients with the various forms of glaucoma.

Given below are some examples illustrating the present method of neurosurgical treatment of glaucoma.

EXAMPLE 1

Female patient D.O., 64. Has been suffering from unilateral open-angle glaucoma for the last five years. According to neurological examination and magnetic-resonance imaging data, there appear signs of cerebral atherosclerosis, in particular, stenosis of *arteria basilaris*. Patient had sustained two ophthalmologic surgeries 4.5 and 1.5 years previously aimed at improving the outflow of the aqueous humour from the eyeball. Both of the operations were conducted using microsurgical instruments and facilities produced but transient stabilization of patient's visual acuity, the first operation at the level of 0.5 and the second, 0.2.

The patient was maintained on antiglaucomatous drops for reducing intraocular pressure, but without any perceptible clinical effect. Ocular fundus data: signs of gradually increased atrophy of the optic nerve appearing as blurred boundaries of the optic disk, its edematous manifestations and discoloration, ectasis of the retinal veins and, accordingly, hyperemia.

Status on admission: OD visual acuity −0.1 to 0.2; incomplete atrophy of the right optic disk. Magnetic-resonance imaging data: right orbit—presence of an increased activity signal from the perieyeball fat under T2 conditions and absence of such signal in the left orbit. OD: an increased diameter of the optic nerve and its impaction into the optic canal. The patient was suggested a surgical treatment according to the present method on account of complete futility of a prolonged traditional surgical and medicinal treatment.

On Oct. 12, 1998 a surgery was performed, under general anesthesia, for osteoplastic trepanation in the right frontal region. There was carried out an extradural approach to the superior orbital wall, followed by its resection trepanation to obtain an oval hole measuring 3×4 cm in order to establish an immediate anastomosis between the edematous perieyeball fat and the exterior dural surface. Finally, an osseous graft was laid on site, whereupon skin stitches were applied.

The operative wound healed normally. No complications secondary to said neurosurgical intervention were observed. The magnetic-resonance imaging of the orbits performed in six months after neurosurgical intervention demonstrated reduced intensity of increased activity signal in the right orbit expressed in absolute values and virtually complete restoration of the diameter of the intracanalicular optic nerve portion. Dynamic control over visual functions of the patient performed for 2.5 years following said neurosurgical intervention demonstrated stabilization of visual acuity at 0.1, ceasing further progressive atrophy of the optic disk on the ocular fundus.

EXAMPLE 2

Male patient M., 59; has been suffering for the last six years from narrow-angle glaucoma. Had sustained two microsurgical interventions by laser iridotomy on the left eyeball. However, a positive effect attained was but transient, that is, visual acuity following the first surgery was stabilized at 0.4, that after the second surgery, at 0.4. Concurrently the patient was administered eye drops reducing intraocular pressure. Status on admission: visual acuity OS: 0.1. Signs of partial atrophy of the optic disk on the ocular fundus, appearing as an incipient optic disk discoloration, slight edema of said disk, phlebectasis and arterial stenosis.

The signs of cerebral atherosclerosis were corroborated both clinically and paraclinically.

In view of ineffectiveness of the previously performed treatment the patient was suggested for a neurosurgical treatment using the herein disclosed.

The patient was subjected to surgery for osteoplastic trepanation in the left frontal region by way of extradural approach to the superior orbital wall, i.e., the base of the anterior cranial fossa, i.e., the orbital roof. Then the aqueous humour was made to flow out by performing resection trepanation of the superior orbital wall in order to establish a contact between the edematous perieyeball fat and the dural surface which was attained due to making a burr hole in the central projection of the superior orbital wall followed by enlarging said hole using bone nippers until the burr hole measured 2.5×3.2×2.5 cm. As a result, the edematous perieyeball fat was free to prolapse into the osseous defect. It was due to profuse bleeding from the perieyeball fat that a hemostatic sponge was put over the prolapsing perieyeball fat in the space confined between the superior orbital wall and the dura mater. Then an ost eoplastic graft was laid on site, and skin stitches were performed.

The postoperative period was uneventful and free from complications. The operative wound healed normally.

Two weeks after the surgery the patient reported a subjective amelioration of visual functions which manifested itself in an improved OS visual acuity. Upon objective examination performed in two months after dismissal, OS visual activity was found to increase to 0.3, the posthyperemic optic papilla was found on the ocular fundus; besides, reduction edema of the optic disk and degree of the retinal phlebectasis were observed.

No antiglaucomatous drugs were administered to the patient during the postoperative period.

EXAMPLE 3

Female patient L., 60. Four years previously right narrow-angle glaucoma was diagnosticated. The patient had sustained two microsurgical interventions involving use of a laser; was also given antiglaucomatous drops and some additional medicines. Despite the treatment given, OD visual acuity continued to drop down to as low as 0.25 diopter; there appeared incipient signs of atrophy of the right optic disk in the form of its discoloration and hyperemia of the retinal veins. Sometimes the glaucomatous process starting on one of the eyeballs in a few years gradually affects the other eyeball. In our opinion, such an event is due to overflow of the aqueous humour through the fibers of the optic nerve towards the optic chiasmus and further along the same path to the other eyeball, thereby contributing to the development of the glaucomatous process in the previously intact eye.

Within the last three months prior to admission to the clinic the patient noted a decrease in OS visual acuity (as compared to earlier Vis OS=1.0–0.9). When studying the patient's visual functions in our clinic it was found a further reduction of Vis OS down to 0.3 diopter. The observation was regarded as transfer of the glaucomatous process to the other eye.

A magnetic-resonance imaging involving displaying the picture of both orbits detected an increased diameter of the intraorbital optic nerve portion (S>D) and a bilateral increase in the MRI-signal from the perieyeball fat (S>D).

The patient was advised to have surgery on the superior orbital wall of both eyeballs at the same time.

An integral-block osteoplastic trepanation in the right frontal region was performed with the base facing the frontotemporal region. There was carried out a consecutive extradural approach first to the right superior orbital wall, followed by enlarging the burr hole until it measures 2.5× 3.0×2.0 cm, then to the left superior orbital wall and enlarging the burr hole until it measures 2.5×3.5×2.0 cm. Hence an outflow of the aqueous humour is effected due to a resection trepanation of the superior orbital wall and establishing a contact between the edematous perieyeball fat and the dural surface. Finally, an bilateral osteoplastic graft was laid on site and affixed, whereupon skin stitches were applied.

The postoperative period was uneventful and free from any complications.

Three months after the patient's dismissal from the clinic it was found the visual functions of both eyes had undergone the following changes: Vis OD=0.2 diopter exhibiting the signs of a certain regression of the pathological picture observed on the ocular fundus earlier. Vis OS=0.6–0.7 which means a considerable amelioration.

Hence visual function in OD (right eye) after the surgery stabilized after said neurosurgical intervention at the preoperative level with a slight regression of the pathological symptoms on the ocular fundus. Visual function in OS (left eye) improved considerably which is evidenced by an increase in visual acuity from 0.3 to 0.6–0.7. Most likely an earlier surgical intervention in the left eyeball promoted fast restoring of visual acuity in OS without developing irreversible hyperemic manifestations on the ocular fundus.

EXAMPLE 4

Male patient M., 68 has been suffering from narrow-angle glaucoma for the last decade. Sustained two microsurgical interventions for laser iridotomy on the left eyeball. However, a positive postoperative effect was but transient. Concurrently the patient received eye drops reducing intraocular pressure. Status on admission: Vis OS=0.1. Signs of partial atrophy of the optic disk on the ocular fundus, appearing as an incipient optic disk discoloration, slight edema of said disk, phlebectasis and arterial stenosis.

In view of ineffectiveness of the previously performed treatment the patient was recommended for neurosurgical treatment using the herein disclosed method.

The patient was subjected to surgery for osteoplastic trepanation in the left frontal region by way of extradural approach to the base of the superior orbital wall. Then a burr hole was made in the central projection of the superior orbital wall followed by enlarging said hole using bone nippers until the burr hole measured 2.5×3.2×2.5 cm. As a result, the edematous perieyeball fat was free to prolapse into the osseous defect. Next a hemostatic sponge was put over the prolapsing perieyeball fat. Finally, an osseous graft was laid on site, and skin stitches were applied.

The postoperative period was uneventful and free from complications. The operative wound healed by first intention.

Two weeks after the surgery the patient noted a subjective amelioration of visual functions which manifested itself in an improved OS visual acuity. Upon objective examination performed in three months after dismissal, OS visual activity was found to increase to 0.3, besides, reduced edema of the optic disk and degree of the retinal phlebectasis were observed. The ocular fundus exhibited the signs of regression of atrophy of the optic nerve.

Hence clinical trial testing of the present invention allows of making conclusion that the proposed method for neurosurgical treatment of glaucoma by establishing a new path for the aqueous humour to flow out beyond the limits of the eyeball with an adequate aqueous humour draining area there is provided stabilization of the clinical picture of atrophy of the optic nerve or of its regression accompanied by enhanced visual functions (i.e., visual activity and field of vision) which makes it possible to attained higher glaucoma treatment efficacy.

What is claimed is:

1. A method for treating glaucoma, comprising the consecutive steps of:
    a) performing osteoplastic trepanation in the frontal region above the affected eyeball;
    b) effecting an extradural approach to the superior orbital wall;
    c) effecting an outflow of the aqueous humour by performing resectiontrepanation of said superior orbital wall so as to establish a contact between the edematous perieyeball fat and the dural surface.

2. The method according to claim 1, wherein after performing said resection trepanation of the superior orbital wall, a biological protector is put in the space confined between said superior orbital wall and the dura mater.

3. The method according to claim 1, wherein prior to performing said osteoplastic trepanation in the frontal region over the affected eyeball the condition of the patient is established using magnetic-resonance imaging.

* * * * *